United States Patent
Hadry et al.

(10) Patent No.: US 7,625,852 B2
(45) Date of Patent: Dec. 1, 2009

(54) NAIL POLISH REMOVER

(76) Inventors: Henry Hadry, P.O. Box 40077, Philadelphia, PA (US) 19106-0077; Everett Farr, P.O. Box 1025, Langhorne, PA (US) 19047-6025

(*) Notice: Subject to any disclaimer, the term of this patent is extended or adjusted under 35 U.S.C. 154(b) by 231 days.

(21) Appl. No.: 11/759,089

(22) Filed: Jun. 6, 2007

(65) Prior Publication Data

US 2007/0287647 A1  Dec. 13, 2007

Related U.S. Application Data

(60) Provisional application No. 60/811,511, filed on Jun. 7, 2006.

(51) Int. Cl.
*C11D 7/26* (2006.01)
*C11D 7/32* (2006.01)
*C11D 7/50* (2006.01)

(52) U.S. Cl. .................. 510/118; 510/499; 510/505

(58) Field of Classification Search ............ 510/118, 510/499, 505
See application file for complete search history.

(56) References Cited

U.S. PATENT DOCUMENTS

| | | | |
|---|---|---|---|
| 2,148,862 A * | 2/1939 | Kern | 106/14.39 |
| 3,939,294 A | 2/1976 | Fieldhouse | |
| 4,255,826 A | 3/1981 | Boyd | |
| 4,309,303 A | 1/1982 | Boyce | |
| 4,321,936 A | 3/1982 | Chaconas | |
| 4,485,037 A | 11/1984 | Curtis | |
| 4,543,206 A | 9/1985 | Adams | |
| 4,804,486 A | 2/1989 | Day | |
| 4,824,662 A | 4/1989 | Hofmann | |
| 5,063,049 A | 11/1991 | Billings | |
| 5,077,038 A | 12/1991 | Hofmann | |
| 5,173,288 A | 12/1992 | Everhart et al. | |
| 5,342,536 A | 8/1994 | Miner et al. | |
| 5,346,652 A | 9/1994 | Dotolo et al. | |
| 5,372,742 A | 12/1994 | Bayless | |
| 5,486,305 A | 1/1996 | Faryniarz et al. | |
| 5,489,610 A | 2/1996 | Fung et al. | |
| 5,646,181 A | 7/1997 | Fung et al. | |
| 5,866,104 A | 2/1999 | Cataneo et al. | |
| 6,028,040 A | 2/2000 | Jarema | |
| 6,071,865 A | 6/2000 | Pickering et al. | |
| 6,210,839 B1 * | 4/2001 | Gan et al. | 429/307 |
| 6,225,269 B1 | 5/2001 | Baker | |
| 6,841,523 B1 | 1/2005 | Holtz | |
| 6,998,371 B2 | 2/2006 | Tavares | |
| 7,074,746 B2 | 7/2006 | Fujii | |
| 2005/0271596 A1 * | 12/2005 | Friedman et al. | 424/45 |

FOREIGN PATENT DOCUMENTS

JP  2003089642 A  3/2003

OTHER PUBLICATIONS

Isobutyl Nitrite, NTP Chemical Repository, Radian Corporation, Aug. 29, 1991.
Woker, The Relations Between Structure and Smell in Organic Compounds, 1978.

* cited by examiner

*Primary Examiner*—Gregory R Del Cotto
(74) *Attorney, Agent, or Firm*—Amin Talati, LLC

(57) ABSTRACT

The present invention provides a nail polish remover comprising isobutyl nitrite and butylated linseed oil as active ingredients for nail polish removal, conditioning and adhesion promotion.

19 Claims, No Drawings

NAIL POLISH REMOVER

This application claims priority under 35 U.S.C 119(e) to 60/811,511, filed Jun. 7, 2006.

FIELD OF THE INVENTION

The present invention relates to an ethyl acetate, acetone and/or acetonitrile-free nail polish remover containing isobutyl nitrite and butylated linseed oil for removing nail polish, conditioning nails, and promoting adhesion.

BACKGROUND OF THE INVENTION

The practice of tinting, coloring, lacquering or polishing finger and/or toe nails has been around for centuries. Typically, nail polish or lacquer products are applied as a temporary decoration and/or to improve the strength of the underlying nail. One advantage of such temporary color applications is that they may be readily removed such that the color or decoration may be changed or so that the natural nail appearance can be restored. Generally, the nail polishes or lacquers are removed using commercially available solvents in the form of nail polish removers.

Currently, nail polish removers generally contain acetone, acetonitriles, benzene, aromatic nitrites, alcohol and/or ethyl acetate as the active ingredient. These nail polish removers are highly toxic and extremely odorous. They can also be harmful, irritating, drying and damaging to the skin and nails when applied for removing nail polish. Accordingly, there is a demand for a nail polish remover which has a reduced level of toxicity and a more pleasing odor.

Additionally, over the last few years, the application of artificial nails such as, for example, acrylic, gel or silk, linen or fiberglass wraps, has become more prevalent. Generally, such products are applied or bonded onto the natural nail to provide a more uniform and/or attractive appearance. Thereafter, a nail polish or lacquer is applied to provide color and/or to cover the sculpting product used to form the artificial nail. Unfortunately, changing or removing a colored polish or lacquer from artificial nails can be difficult since most commercially available nail polish removers may damage the underlying sculpting product. For example, solvents such as acetates, acetones and acetonitriles which are commonly used in nail polish removers can weaken and/or dissolve the resins or sculpting products used to form and/or bond the artificial nail to the natural nail. Thus, there is a demand for a nail polish remover that can be applied on or used to remove polish from artificial nails without damaging or compromising the integrity of the resins or sculpting products used to form the artificial nail.

SUMMARY OF THE INVENTION

A general object of the present invention is to provide a nail polish remover that is ethyl acetate, acetone and/or acetonitrile-free.

A more specific object of the invention is to overcome one or more of the problems described above.

Another object of the present invention is to provide a nail polish remover that is less and/or non-malodorous.

A further object of the present invention is to provide a nail polish remover with a reduced level of toxicity.

An even further object of the present invention is to provide a nail polish remover that decomposes at a slower rate than the typical commercially available nail polish removers and promotes adhesion.

The general object of the invention can be obtained, at least in part, through a nail polish remover containing an alkyl nitrite solvent and a hygroscopic stabilizer.

The prior art generally fails to provide a nail polish remover which is as effective as may be desired for removing nail polish, conditioning nails, and/or promoting adhesion. Further, the prior art generally fails to provide a nail polish remover having a desirable odor and having a reduced level of toxicity.

Accordingly, Applicants have developed a nail polish remover which is less and/or non-malodorous, has a reduced level of toxicity compared to typical commercially available nail polish removers, and is ethyl acetate, acetone and/or acetonitrile-free.

The nail polish remover in accordance with the present invention includes isobutyl nitrite and butylated linseed oil and has been developed to be substantially free of ethyl acetate, acetone, acetonitrile or combinations thereof and is in a liquid form specifically for the purpose of removing nail polish, conditioning nails, and promoting adhesion.

In another embodiment of the present invention, the nail polish remover includes about 80% to about 95% by volume isobutyl nitrite and about 0.25% to about 2% by volume butylated linseed oil wherein the nail polish remover has a vapor phase including less than about 600 ppm isobutyl nitrite.

In still another embodiment of the present invention, the nail polish remover may be used on natural nails or artificial nails.

The present invention also relates to a method of removing nail polish from a human nail or artificial nail utilizing a nail polish remover including isobutyl nitrite and butylated linseed oil as active ingredients. The present invention also relates to a kit containing the nail polish remover and an instruction for administering the nail polish remover onto a human nail or artificial nail.

These and other embodiments of the present invention are more fully described in connection with the detailed description.

DETAILED DESCRIPTION OF THE INVENTION

The nail polish remover of one form of the present invention removes nail polish, conditions nails, and promotes adhesion. The nail polish remover is designed to be ethyl acetate, acetone and/or acetonitrile-free, less and/or non-malodorous and/or having a reduced level of toxicity compared to typical commercially available nail polish remover products. As discussed above, many traditional or commercially available nail polish remover products contain solvents which can have a relatively strong and/or unpleasant odor. Further such nail polish remover products may be drying and/or damaging to natural and/or artificial nails.

In accordance with the present invention, a nail polish remover composition includes or consists of an alkyl nitrite solvent and a hygroscopic stabilizer. Suitably, the nail polish remover includes about 10% to about 95% by volume alkyl nitrite solvent and about 0.25% to about 2% by volume hygroscopic stabilizer. Suitably, the nail polish remover can be used on natural and/or artificial nails including, but not limited to, sculptured, acrylic, gel and/or fiber wrapped artificial nails and nail tips. Further, nail polish removers in accordance with the present invention can be substantially free of ethyl acetate, acetone and/or acetonitrile solvents. As used herein, the terms "free" or "substantially free" refer to compositions or formulations containing or comprising less than about 1% by volume of the recited ingredient, solvent or chemical.

One alkyl nitrite solvent suitable for use in the present application is isobutyl nitrite. Isobutyl nitrite has the chemical formula $C_4H_9NO_2$ and can be alternatively referred to as nitrous acid, isobutyl ester; nitrous acid, 2-methylpropyl ester; and IBN. Isobutyl nitrite is very stable and has a moderate toxicity level. In particular, isobutyl nitrite has an inhalation toxicity level of about 600 ppm in vapor which makes it less toxic than previous nail polish removers. For example, acetonitrile, which has an inhalation toxicity level of about 60 ppm in vapor, is ten times more toxic than isobutyl nitrite. Thus, in accordance with certain embodiments, a vapor phase of the nail polish remover suitably includes less than about 600 ppm isobutyl nitrite.

Additionally, isobutyl nitrite has a pleasant and fruity odor. The pleasant and fruity odor makes the present invention less and/or non-malodorous when compared to traditional or typical commercially available nail polish remover products. The isobutyl nitrite in the present invention further advantageously provides solvent integrity and strength. The isobutyl nitrite in the present invention also promotes adhesion of an artificial nail during the application or bonding of the artificial nail to a natural nail and promotes adhesion of the nail polish or lacquer to a natural or artificial nail due to its potency.

In another embodiment of the present invention, the nail polish remover includes isobutyl nitrite that is greater than or equal to about 20% pure isobutyl nitrite. In another embodiment of the present invention, the nail polish remover includes isobutyl nitrite that is greater than or equal to about 50% pure isobutyl nitrite.

In another embodiment of the present invention, the nail polish remover includes at least about 80% to about 95% by volume isobutyl nitrite.

Other alkyl nitrite solvents suitable for use in the present application are nitrited cyclic alcohols, such as, but not limited to cyclohexyl nitrite, and cyclopentyl nitrite, and alkyl alcohols, such as, but not limited to isopentyl nitrite, isopropyl nitrite, and isohexyl nitrite.

Nail polish removers in accordance with the present invention additionally include a hygroscopic stabilizer. Such hygroscopic stabilizers advantageously reduce or prevent decomposition or degradation of the nail polish remover and/or individual components or ingredients in the nail polish remover upon exposure to aqueous media. Suitably the nail polish remover includes or contains about 0.25% to about 2% by volume hygroscopic stabilizer.

In accordance with certain embodiments, the hygroscopic stabilizer can include or be butylated linseed oil. Butylated linseed oil hygroscopically stabilizes the nail polish remover of the present invention by reducing the rate of decomposition of the alkyl nitrite solvent upon exposure to moisture which maintains the shelf life. The butylated linseed oil also maintains the integrity and solvent strength of the nail polish remover of the present invention, which may be diluted by water.

Another hygroscopic stabilizer suitable for use in the present invention is an activated alumina pellet which is in bottle solution about ⅛ to about ¼ inch in diameter.

In another embodiment of the present invention, the nail polish remover includes at least about 0.25% to about 2% by volume butylated linseed oil. In another embodiment of the present invention, the nail polish remover includes butylated linseed oil that is greater than or equal to about 1% by volume butylated linseed oil.

In accordance with certain embodiments, the nail polish remover can additionally include one or more inactive ingredients and/or ingredients which provide additional beneficial attributes to the nail polish remover. Such additional ingredients include, but are not limited to sodium bicarbonate, silicone, isobutyl alcohol, calcium chloride, and water.

In one embodiment of the present invention, the nail polish remover includes about 90% by volume isobutyl nitrite and about 1% by volume butylated linseed oil.

In accordance with one embodiment, the nail polish remover includes about 90% by volume isobutyl nitrite, about 1% by volume butylated linseed oil, about 9.5% by volume isobutyl alcohol, and about 0.5% by volume silicone.

In accordance with one embodiment, the nail polish remover includes about 87% by volume isobutyl nitrite, about 1% by volume butylated linseed oil, about 12.75% by volume isobutyl alcohol, and about 0.25% by volume silicone.

In accordance with one embodiment, the nail polish remover includes about 85% by volume isobutyl nitrite, about 1% by volume butylated linseed oil, about 14.75% isobutyl alcohol, and about 0.25% by volume silicone.

In one embodiment of the present invention, the nail polish remover is liquid. The nail polish remover may be administered or dispensed onto the nails through the use of a cotton ball, cotton swab, cotton swab attached to a plastic sleeve containing glass ampoule, or similar tool.

The present invention also relates to a method of removing nail polish which includes administering a nail polish remover comprising isobutyl nitrite and butylated linseed oil as active ingredients onto a human nail or artificial nail. One form of the method of removing nail polish utilizes the nail polish remover described above and includes administering the nail polish remover onto a human nail or artificial nail through the use of a cotton ball or similar tool; and rubbing the cotton ball containing nail polish remover on the human nail or artificial nail until the nail polish has been removed.

The present invention also relates to a kit containing a nail polish remover having isobutyl nitrite and butylated linseed oil as active ingredients and an instruction for a human to administer the nail polish remover onto a human nail or artificial nail. One form of the kit includes the nail polish remover described above and an instruction for a human to administer the nail polish remover onto nails by utilizing a cotton ball to administer the nail polish remover onto the human nail or artificial nail and rubbing the cotton ball containing nail polish remover on the human nail or artificial nail until the nail polish has been removed.

The present invention also includes a method of producing the nail polish remover. The method includes charging a vessel with isobutyl alcohol and agitating; adding de-ionized water which is 10% by weight of the isobutyl alcohol; chilling to 10° C.; maintaining a maximum temperature of 10° C.; adding sodium nitrite; slowly adding hydrochloric acid; agitating for ten minutes; allowing to stand for 30 minutes for solution separation; removing the water and salt solution; adding sodium bicarbonate and de-ionized water; agitating for 10 minutes; removing the water and sodium bicarbonate solution; slowly agitating and charging with calcium chloride for 25 minutes; removing the calcium chloride; removing the isobutyl nitrite and weighing; charging the vessel with isobutyl nitrite solution; agitating; charging the vessel with butylized linseed oil and agitating for 5 minutes; removing the solution and placing in airtight containers containing nitrogen bath and activated alumina pellets; and adding silicone.

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention.

We claim:

1. A nail polish remover, comprising:
   an alkyl nitrite solvent; and
   a hygroscopic stabilizer comprising butylated linseed oil.

2. The nail polish remover in accordance with claim 1, wherein the alkyl nitrite solvent comprises isobutyl nitrite.

3. The nail polish remover in accordance with claim 1, wherein the alkyl nitrite solvent is chosen from the group consisting of cyclohexyl nitrite, cyclopentyl nitrite, isopentyl nitrite, isopropyl nitrite, and isohexyl nitrite.

4. The nail polish remover in accordance with claim 1, wherein the alkyl nitrite solvent comprises greater than or equal to about 20% pure isobutyl nitrite.

5. The nail polish remover in accordance with claim 1, wherein the alkyl nitrite solvent comprises greater than or equal to about 50% pure isobutyl nitrite.

6. The nail polish remover in accordance with claim 1, wherein the alkyl nitrite solvent comprises about 80% to about 95% by volume isobutyl nitrite.

7. The nail polish remover in accordance with claim 2, wherein a vapor phase of the nail polish remover comprises less than about 600 ppm isobutyl nitrite.

8. The nail polish remover in accordance with claim 1, wherein the nail polish remover is liquid.

9. The nail polish remover in accordance with claim 1, wherein the nail polish remover can remove nail polish from human nails or artificial nails.

10. A nail polish remover comprising:
    isobutyl nitrite; and
    butylated linseed oil,
    wherein the nail polish remover is substantially free of ethyl acetate, acetone, acetonitrile or combinations thereof.

11. The nail polish remover in accordance with claim 10 comprising at least about 10% by volume isobutyl nitrite.

12. The nail polish remover in accordance with claim 10, wherein a vapor phase of the nail polish remover comprises less than about 600 ppm isobutyl nitrite.

13. The nail polish remover in accordance with claim 10 comprising at least about 0.25% by volume butylated linseed oil.

14. A nail polish remover kit comprising:
    the nail polish remover in accordance with claim 10; and
    an instruction for administering the nail polish remover onto a human nail or artificial nail.

15. A nail polish remover, comprising:
    about 80% to about 95% by volume isobutyl nitrite; and
    about 0.25% to about 2% by volume butylated linseed oil,
    wherein the nail polish remover has a vapor phase including less than about 600 ppm isobutyl nitrite.

16. The nail polish remover in accordance with claim 15 further comprising silicone.

17. The nail polish remover in accordance with claim 16 comprising about 0.25% to about 0.5% by volume silicone.

18. The nail polish remover in accordance with claim 15 further comprising isobutyl alcohol.

19. The nail polish remover in accordance with claim 18 comprising about 4.5% to about 19.75% by volume isobutyl alcohol.

* * * * *